United States Patent
Sela

(10) Patent No.: US 8,062,666 B2
(45) Date of Patent: Nov. 22, 2011

(54) EXTENDED RELEASE COMPOSITIONS COMPRISING AS ACTIVE COMPOUND VENLAFAXINE HYDROCHLORIDE

(75) Inventor: Yoram Sela, Raanana (IL)

(73) Assignee: Lycored Bio Ltd., Yavne (IL)

( * ) Notice: Subject to any disclaimer, the term of this patent is extended or adjusted under 35 U.S.C. 154(b) by 66 days.

(21) Appl. No.: 10/500,634

(22) PCT Filed: Nov. 7, 2002

(86) PCT No.: PCT/IL02/00890
§ 371 (c)(1),
(2), (4) Date: Jan. 24, 2005

(87) PCT Pub. No.: WO03/041692
PCT Pub. Date: May 22, 2003

(65) Prior Publication Data

US 2005/0118264 A1   Jun. 2, 2005
US 2010/0330178 A2   Dec. 30, 2010

(30) Foreign Application Priority Data

Nov. 13, 2001   (IL) .......................................... 146462

(51) Int. Cl.
A61K 9/26 (2006.01)
A61K 31/277 (2006.01)

(52) U.S. Cl. ........................................ 424/468; 514/522

(58) Field of Classification Search .................. 424/468
See application file for complete search history.

(56) References Cited

U.S. PATENT DOCUMENTS

| | | | |
|---|---|---|---|
| 4,389,393 A | 6/1983 | Schor et al. | |
| 4,521,401 A | 6/1985 | Dunn | |
| 4,786,505 A | 11/1988 | Lovgren et al. | |
| 4,966,768 A | 10/1990 | Michelucci et al. | |
| 5,232,706 A * | 8/1993 | Palomo Coll | 424/475 |
| 5,472,712 A * | 12/1995 | Oshlack et al. | 424/480 |
| 5,505,983 A * | 4/1996 | Kamada | 427/2.21 |
| 6,149,943 A * | 11/2000 | McTeigue et al. | 424/494 |
| 6,274,171 B1 | 8/2001 | Sherman et al. | |
| 6,403,120 B1 | 6/2002 | Sherman et al. | |
| 6,419,958 B2 | 7/2002 | Sherman et al. | |
| 6,451,350 B1 | 9/2002 | Bartholomaeus et al. | |
| 6,660,300 B1 | 12/2003 | Timmins et al. | |
| 6,703,044 B1 | 3/2004 | Pinhasi et al. | |
| 7,563,456 B2 | 7/2009 | Rafael De Souza et al. | |
| 7,807,195 B2 | 10/2010 | Bhattacharya et al. | |
| 2003/0190354 A1 | 10/2003 | Sela | |
| 2005/0169985 A1 | 8/2005 | Bhattacharya et al. | |
| 2006/0121114 A1 | 6/2006 | Antarkar et al. | |
| 2006/0182797 A1 | 8/2006 | Karavas et al. | |
| 2009/0081286 A1 | 3/2009 | Dixit et al. | |

FOREIGN PATENT DOCUMENTS

| | | |
|---|---|---|
| CA | 2529393 | 8/2010 |
| EP | 0797991 | * 10/1997 |
| EP | 0797991 A1 | 10/1997 |
| EP | 0919236 | * 2/1999 |
| EP | 0 919 236 A1 | 6/1999 |
| WO | 94 27589 A2 | 12/1994 |
| WO | EP 0919236 A1 * | 5/1998 |
| WO | WO 99/22724 A2 | 5/1999 |
| WO | WO 9922724 A2 * | 5/1999 |
| WO | WO 00/71099 A1 * | 11/2000 |
| WO | WO 0071099 A1 * | 11/2000 |
| WO | 01/19901 | 3/2001 |
| WO | 02 102129 A2 | 12/2002 |
| WO | 03 041692 A1 | 5/2003 |
| WO | 2004/047718 A2 | 6/2004 |
| WO | 2004/091580 A1 | 10/2004 |
| WO | 2005/009414 A1 | 2/2005 |
| WO | 2005/034930 A1 | 4/2005 |
| WO | 2005/074895 A1 | 8/2005 |

OTHER PUBLICATIONS

FDA (Guidance for Industry. Bioavailability and bioequivalence studies for orally administered drug products—General considerations (2002).*
Dorland's Illustrated Medical Dictionary, 29th ed., Philadelphia, PA, W.B. Saunders Co, p. 599 (2000).
Dorland's Illustrated Medical Dictionary, 29th ed., Philadelphia, PA, W.B. Saunders Co, p. 636 (2000).
Ghebre-Sellassie "Multiparticulate oral drug delivery", Drugs and the pharmaceutical sciences; v. 65 Chapters 5 and 10, pp. 78-111 and 218-283 (1994).
Colorcon publication "Surelease" (1990).
Porter et al. "Use of Opadry, Sureteric, and Surelease for the Aqueous Film Coating of Pharmaceutical Oral Dosage Forms" Aqueous Polymeric Coatings for Pharmaceutical Dosage Forms / Drugs and the pharmaceutical sciences, Second Edition, Revised and Expanded, Marcel Dekker, Inc. v. 79, Chapter 9, pp. 327-372 (1997).
Ethocel Ethylcellulose Polymers Technical Handbook, Dow Cellulosics (2004).
Methocel Cellulose Ethers resources, Chemistry, Typical Chemical Structures of METHOCEL Products, Dow, http://www.dow.com/methocel/resource/chem.htm (downloaded Aug. 18, 2010).

(Continued)

Primary Examiner — Jake M. Vu
(74) Attorney, Agent, or Firm — Browdy and Neimark, PLLC

(57) ABSTRACT

The present invention relates to an extended release composition comprising as active compound Venlafaxine Hydrochloride, in which Venlafaxine Hydrochloride is coated on a non pareil inert core, which coated core is then coated with polymeric layer which enables the controlled release of the Venlafaxine Hydrochloride.

2 Claims, No Drawings

OTHER PUBLICATIONS

Eudragit RL 30 D Online Publication, Evonik Industries, http://eudragit.evonik.com/product/eudragit/en/products-services/eudragit-products/sustained-release-formulations/rl-30-d/pages/default.aspx (downloaded Aug. 17, 2010).

Eudragit RS 30 D Online Publication, Evonik Industries, http://eudragit.evonik.com/product/eudragit/en/products-services/eudragit-products/sustained-release-formulations/rs-30-d/pages/default.aspx (downloaded Aug. 17, 2010).

(GMS) Mono-And Diglycerides, Prepared at the 17th JECFA (1973), published in FNP 4 (1978) and in FNP 52 (1992). Metals and arsenic specifications revised at the 55th JECFA (2000).

Orange Book: Approved Drug Products with Therapeutic Equivalent Evaluations., (Venlafaxine Hydrochloride) FDA online book: http://www.accessdata.fda.gov/scripts/cder/ob/default.cfm (downloaded Aug. 18, 2010).

Non-Final Office Action of Aug. 22, 2005, in U.S. Appl. No. 10/406,777.

Final Office Action of Apr. 11, 2006, in U.S. Appl. No. 10/406,777.

Non-Final Office Action of Dec. 28, 2006, in U.S. Appl. No. 10/406,777.

Non-Final Office Action of Sep. 20, 2007, in U.S. Appl. No. 10/406,777.

Dias et al., Investigation of a Venlafaxine HCl (37.5 mg) Extended Release Formulation Using Hypromellose (HPMC) Matrices, Methocel Application Data, http://www.colorcon.com [Online] (2006).

Gohel et al., "Advanced formulation design of venlafaxine hydrochloride coated and triple-layer tablets containing hypromellose", Pharmaceutical Development and Technology; 14(6): 650-658 (2009).

Madhavi et al., "Formulation and Evaluation of Venlafaxine HCL Enclosed in Alginate Microbeads Prepared by Iontophoretic Gellation Method" International Journal of Pharma Research and Development, pp. 1-11, Publication Ref No. IJPRD/2009/PUB/ARTI/VOL-8/OCT/006 [Online], (2009).

Makhija et al., Once daily sustained release tablets of venlafaxine, a novel antidepressant. Eur J. Pharm Biopharm, 54(1):9-15 (2002).

Park et al., "Formulation of Sustained Release Granule for Venlafaxine-HCl Using Water-Insoluble Polymer" J. Kor. Pharm, Sci., vol. 37, No. 2, 101-106 (2007).

Public Assessment Report, Decentralised Procedure, "Ranfaxiran XL 37.5 mg, 75 mg and 150 mgprolonged release capsules, hard," "RanfaxineXL 37.5 mg, 75 mg and 150 mg prolonged release, capsules, hard" PL 14894/0519-24, UK/H/1129/01-03DC, UK/H/1130/01-03DC, Medicines and Healthcare Products Regulatory Agency, Ranbaxy (UK) Limited, pp. 1-3, and 19-21 (2008).

Trixat XL 75 MG Prolonged Release Capsules, PL 10622/0280, Trixat XL 150 MG Prolonged Release Capsules, PL 10622/0281, Ukpar, Medicines and Healthcare Products Regulatory Agency, pp. 1-2, 5, 6 and 30-32 (2008).

* cited by examiner

EXTENDED RELEASE COMPOSITIONS COMPRISING AS ACTIVE COMPOUND VENLAFAXINE HYDROCHLORIDE

The present invention relates to extended release compositions comprising as active compound venlafaxine hydrochloride.

Venlafaxine hydrochloride is an antidepressant having formula (1)

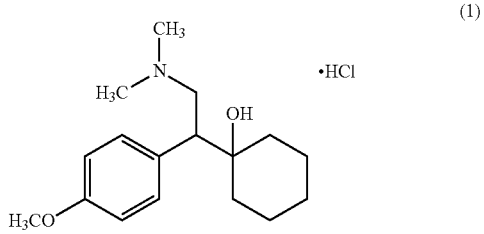

being designated (R/S)-1-[2-(dimethylamino)-1-(4-methoxyphenyl)-ethyl]cyclohexanol hydrochloride or (±)-1-[a](dimethylamino)-methyl]p-methoxybenzyl cyclohexanol hydrochloride, having the empirical formula of $C_{17}H_{27}NO_2$ hydrochloride and molecular weight of 313.87.

Venlafaxine hydrochloride is a white to off-white crystalline solid with a solubility of 572 mg/ml in water (adjustment to ionic strength of 0.2 M with sodium chloride). Its octanol: water (0.2 M sodium chloride) partition coefficient 0.43. EFFEXOR XR, the Brand product, is formulated as an extended release capsule for once-a-day oral administration.

The drug release has so far been controlled by diffusion through the coating membrane on the spheroids and is not pH-dependent. Known capsules containing venlafaxine hydrochloride comprise amounts equivalent to 37.5 mg, 75 mg, or 150 mg of venlafaxine. The inactive ingredients are mainly cellulose, ethylcellulose, gelatin, hydroxypropylmethylcellulose, iron oxide, and titanium dioxide.

Controlled or extended release dosage forms of medicament are conventionally produced as hydrogel matrix-based tablets. With this technology, the controlled release dosage forms are simply prepared by mixing the active material with the appropriate rate of controlling polymers and then that mixture is compressed into the desired controlled release tablets. The rate-controlling polymers are normally termed as hydrogels. Examples of such polymers are cellulose ethers such as ethyl cellulose or hydroxypropylcellulose. Patents describing preparation methods of such dosage forms are described, for example, in US Patent Specifications 4,966,768 and 4,389,393.

In some cases, for example with very water soluble active materials and with relatively high doses, it is not feasible to produce tablets which enable appropriate control on the drug's release. This is the case, for example with venlafaxine hydrochloride.

In such a case, a suitable approach is encapsulating the drug and producing extended release capsule dosage forms. When preparation of such dosage forms is considered, the preferred way is to mix the active ingredient with at least one binding agent to form a uniform mixture which is later moistened with water or with an appropriate organic solvent to form an extrudable plastic mass, from which small particles, cylindrical in shape (1 mm diameter), of drug/matrix are extruded, chopped into appropriate lengths and converted to spheroids using spheronization equipment. These spheroids are further dried and then film-coated with an appropriate polymer to form a film with the desired release patterns. The most widely used excipient in the extruding process is microcrystalline cellulose in its different grades; usually, water is used for the wetting process.

Polymers widely used for coating are ethyl cellulose or EUDRAGIT (ammonio methacrylate copolymer, type A or B). Water-soluble ingredients are normally mixed with the ethyl cellulose or with other hydrophobic polymers, such as pore forming agents, to assist the control on the drug's release through the hydrophobic coating layer. The water-soluble ingredients, such as hydroxypropylcellulose or polyethylene glycol, may serve as plasticizers as well.

Venlafaxine hydrochloride has so far been formulated into a controlled release dosage form with the ability to provide in a single dose a therapeutic blood serum level of the drug over a twenty four hour period. By this method, tighter plasma therapeutic range control can be obtained and multiple dosing is avoided in this manner. The sharp peaks and troughs in blood plasma drug levels are avoided as well.

With the conventional release dosage forms of venlafaxine hydrochloride (tablets), peak blood plasma levels appeared after 2-4 hrs, in contrast to the extended release dosage forms, when plasma levels of venlafaxine hydrochloride rose after administration for between five to eight hrs (average–6) and then begin to fall through a protracted, substantially linear decrease from the peak plasma level for the reminder of the period, maintaining therapeutic level of the drug during the entire twenty four hours period.

In WO 99/22724 (AHP, Sherman), a detailed description of preparing an encapsulated dosage form (coated spheroids) of venlafaxine hydrochloride is provided. By the method described therein, a spheroid core is prepared by extruding and spheronizing a mixture of the drug with microcrystalline cellulose, and then coating it with an ethyl cellulose hydroxypropylcellulose mixture.

This dosage form provides an extended release product with the following in vitro dissolution specifications:

| Time (hrs) | Average % venlafaxine HCL release |
| --- | --- |
| 2 | <30 |
| 4 | 30-55 |
| 8 | 55-80 |
| 12 | 65-90 |
| 24 | >80 |

These dissolution characteristics are pH- and RPM-independent.

In the present invention, an alternative once daily bioequivalent formulation to the innovator's one (EFFEXOR XR, described in WO 99/22724) has been developed.

As already mentioned, with high dose water-soluble product, such as venlafaxine hydrochloride (150 mg), the usual preferred way of encapsulating it is by preparing and coating appropriate beads, using the extrusion spheronization process.

In the present invention, the microencapsulation has been changed, i.e., is being performed by layering the drug over an inert nonpareil core, and then coating it with an appropriate polymeric mixture.

The present invention thus consists in an extended release composition comprising as active compound venlafaxine hydrochloride, in which venlafaxine hydrochloride is coated on a nonpareil inert core, which coated core is then coated with a polymeric layer which enables the controlled release of the venlafaxine hydrochloride.

The composition preferably comprises 30-60% of venlafaxine hydrochloride per weight of the total dosage form.

In a preferred embodiment of the present invention, the venlafaxine hydrochloride is suitably connected to a binder; said binder may be, e.g., polyvinylpyrrolidone (povidone), hydroxypropylcellulose, hydroxypropylmethylcellulose, etc. The composition preferably comprises 0.5%-10% of the binder per weight of the total dosage form.

Advantageously the nonpareil inert core is an inert sugar core, a microcrystalline cellulose, or the like. The composition preferably comprises 30-60% of the core per weight of the total dosage form.

Alternatively, the drug might be sprayed as it is and the water is then used as binding enhancement agent.

Advantageously, the coated core is coated with an isolating/protecting/separating layer, which layer is suitably composed of polymers such as polyvinylpyrrolidone, hydroxypropylcellulose, hydroxypropylmethylcellulose, microcrystalline cellulose, carrageenan, GMS, etc. The composition preferably comprises 0.5-10% of the isolating layer per weight of the total dosage form.

The core or the isolating layer is coated then with an additional polymeric layer which enables the controlled release of venlafaxine hydrochloride. Said additional polymeric layer is composed, e.g., of a hydrophobic polymer mixed with an appropriate hydrophobic or hydrophilic plasticizer. Said polymeric layer is suitably sprayed over the coated nonpareil layer or over the isolating layer.

Appropriate coating polymers are, e.g. EUDRAGIT, cellulose derivatives such as hydroxypropylmethylcellulose, ethyl cellulose, cellulose acetate, etc. Their suitable plasticizers are, e.g., castor oil, dibutyl sebacate, glyceryl monostearate, diethyl phthalate, glyceryl triheptanoate, triethylcitrate, etc.

The coating polymeric layer may also be a wax-based coating.

The composition preferably comprises 2-15% of the hydrophobic polymer per weight of the total dosage form, and preferably 0.1-2% per weight of the hydrophobic plasticizer per weight of the total dosage form.

The above processes are conventional processes that may be performed in a fluidized bed coater with a bottom spraying mechanism.

In the composition according to the present invention, preferably not more than 40% of the drug is released after two hours, not more than 60% released after 4 hours, and not more than 80% after 8 hours.

The compositions obtained are suitably, e.g., filled into hard gelatin capsules or compressed into tablets.

This formulation has an identical in vitro dissolution profile as EFFEXOR XR (see Sherman, WO99/22724). They are not sensitive to any changes in dissolution conditions. It is bioequivalent to EFFEXOR XR 150 mg caps.

The coating process being used to produce the composition according to the present invention is more efficient than the method being used in the Sherman patent. Moreover, it enables the preparation of the drug in a single type of equipment, e.g. a fluidized bed coater.

The present invention will now be illustrated with reference to the following examples, without being limited by them.

The process for preparing the composition according to the present invention is suitably performed as follows (all temperatures are given in degrees centigrade):

a. When venlafaxine hydrochloride is connected to a binder the venlafaxine hydrochloride is connected to the binder by methods known per se.

b. Stage 1

Coating the nonpareil core with the venlafaxine hydrochloride (advantageously connected with a binder) is performed at an inlet temperature of 45-55° (preferably at 50°) at an outlet temperature of 35-45° (preferably at 40°).

At the end of the spraying process, the composition is dried for 10 minutes without nozzle with 30 cfm air flow.

c. Stage 2

The coated core obtained in Stage 1 is coated with the insulating layer at an inlet temperature of 60°+/−3° at an outlet temperature of 50°+/−2°.

d. Stage 3 (when an insulating layer is present in Stage 2)

The core is coated with a further preliminary layer; the conditions of said coating are:

| | |
|---|---|
| Inlet temp: | 50° +/− 2° |
| Outlet temp: | 40° +/− 5° |

EXAMPLE NO. 1

Without Binder

| Stage 1: Components | |
|---|---|
| Nonpareils 25/30 | 150 gr |
| Venlafaxine hydrochloride | 37.5 gr |
| $H_2O$ | 150 gr. |
| Stage 2: Components - 150 gr layered pellets from stage 1 | |
| ETHOCEL 45 cp | 15 gr |
| METHOCEL 5 cp | 1 gr |
| Ethanol BP | 300 gr |

At the end of the spray process the composition is dried for 10 minutes without nozzle with 30 cfm.

EXAMPLE NO. 2

| Stage 1: components | |
|---|---|
| Nonpareils (inert sugar pellets) | 150 gr |
| Povidone K-30 | 3.3 gr. |
| Venlafaxine hydrochloride | 165 gr. |
| Ethanol BP | 670 gr. |
| Stage 2: components - 150 gr. layered pellets from stage 1 | |
| ETHOCEL 45 cp | 15 gr |
| METHOCEL 5 cp | 1 gr |
| Ethanol BP | 300 gr |

The coating process was performed in a "4" fluidized bed coater made by Coating Place Inc. USA.

EXAMPLE NO. 3

| Stage 1: components | |
|---|---|
| Nonpareils 25/30 | 150 gr |
| Venlafaxine hydrochloride | 37.5 gr |
| Povidone K-30 | 0.75 gr |
| Ethanol BP | 160 gr |
| Stage 2: components - 150 gr layered pellets from stage 1 | |
| EUDRAGIT RS 30 D | 150 gr |
| Triethyl citrate | 9 gr |
| Glycerol monostearate | 2.25 gr |
| Polysorbate 80 | 1 gr |
| Water | 140 gr |

The coating process was performed in a "4" fluidized bed coater, made by Coating Place Inc. USA.

EXAMPLE NO. 4

| Stage 1: components | |
|---|---|
| Nonpareils 25/30 | 150 gr. |
| Povidone K-30 | 0.75 gr. |
| Venlafaxine-HCL | 37.5 gr. |
| Ethanol-BP | 160 gr. |
| Stage 2: components - 150 gr. layered pellets from stage 1 | |
| EUDRAGIT RS 30 D | 150 gr. |
| EUDRAGIT RL 30 D | 15 gr. |
| Triethyl citrate | 9 gr. |
| Glycerol monostearate | 2.25 gr. |
| Polysorbate 80 | 1 gr |
| Water | 140 gr. |

All processes were performed in a "4" fluidized bed coater, made by Coating Place Inc. USA.

EXAMPLE NO. 5

| Stage 1: components - 150 gr. Nonpareils 25/30 | |
|---|---|
| Povidene K-90 | 4.5 gr. |
| Venlafaxine-HCL | 150 gr. |
| Ethanol BP | 670 gr. |
| Water | 110 gr |
| Stage 2: components - 150 gr. pellets from stage 1 | |
| Povidone K-30 | 3.75 gr. |
| Ethanol-absolute | 60 gr. |
| Stage 3: components - 150 gr. Pellets from stage 2 | |
| ETHOCEL 100 cp | 8 gr. |
| Dibutyl sebacate | 0.8 gr. |
| Ethanol-absolute | 300 gr. |

In the above examples, EUDRAGIT RS 30 D is poly(ethyl acrylate-co-methyl methacrylate-co-trimethylammonioethyl methacrylate chloride) 1:2:0.1. EUDRAGIT RL 30 D is poly(ethyl acrylate-co-methyl methacrylate-co-trimethylammonioethyl methacrylate chloride) 1:2:0.2. ETHOCEL is ethyl cellulose and METHOCEL is methyl cellulose.

The invention claimed is:

1. A pH-independent extended release dosage form having specified dissolution characteristics, comprising:
venlafaxine hydrochloride in an amount of 30-60% based on the total weight of the dosage form;
said venlafaxine hydrochloride being coated on a nonpareil inert core, said nonpareil inert core comprising 30-60% based on the total weight of the dosage form;
the venlafaxine hydrochloride being optionally connected to a binder in a binder amount of 0.5-10% based on the total weight of the dosage form wherein said binder, when present, is selected from the group consisting of polyvinylpyrrolidone, hydroxypropylcellulose and hydroxypropylmethylcellulose;
an isolating layer coating said venlafaxine hydrochloride and comprising 0.5-10% based on the total weight of the dosage form, said isolating layer being polyvinylpyrrolidone; and
a controlled release layer coated over said isolating layer, said controlled release layer comprising a controlled release polymer mixed with a plasticizer, said controlled release polymer comprising 2-15% based on the total weight of the dosage form, said controlled release polymer being ethyl cellulose, and said plasticizer comprising 0.1-2% based on the total weight of the dosage form, said plasticizer being dibutyl sebacate;
the parameters being selected so as to control release of the venlafaxine hydrochloride over an approximately 24 hour period in a manner that the following pH and rpm independent in vitro dissolution specifications are obtained:

| Time (hrs) | Average % venlafaxine HCl release |
|---|---|
| 2 | <30 |
| 4 | 30-55 |
| 8 | 55-80 |
| 12 | 65-90 |
| 24 | >80. |

2. In a method for administering venlafaxine hydrochloride to a patient in need thereof, comprising administering the venlafaxine hydrochloride as an extended release composition to the patient, the improvement wherein the extended release composition is in accordance with claim 1.

* * * * *